United States Patent [19]

Smith

[11] Patent Number: 5,133,967
[45] Date of Patent: Jul. 28, 1992

[54] TONING COMPOSITION AND PROCESS OF USING

[75] Inventor: Harry A. Smith, Midland, Mich.

[73] Assignee: The Dow Chemical Company, Midland, Mich.

[21] Appl. No.: 719,419

[22] Filed: Jun. 24, 1991

[51] Int. Cl.$^5$ .............................................. A61K 7/48
[52] U.S. Cl. ..................................... 424/401; 424/47; 514/846
[58] Field of Search ............... 514/844, 846, 847, 848, 514/941; 568/679, 623; 424/401, 47; 252/311, 101

[56] References Cited

U.S. PATENT DOCUMENTS

| | | | |
|---|---|---|---|
| 3,652,420 | 3/1972 | Hill | 252/101 |
| 4,246,257 | 4/1981 | Elliott | 424/78 |
| 4,370,319 | 6/1983 | Chapin et al. | 424/184 |
| 4,483,783 | 11/1984 | Albanese | 252/311 |
| 4,788,345 | 8/1988 | Sebag et al. | 568/623 |

FOREIGN PATENT DOCUMENTS 456045  7/1968  Switzerland .

OTHER PUBLICATIONS

Dowanol TM DPM Glycol Ether Use in Cosmetic Formulations 1981, Organic Chemicals.

*Primary Examiner*—Thurman K. Page
*Assistant Examiner*—D. Colucci

[57] ABSTRACT

A toning composition which employs one or more of the propylene and butylene oxide-based glycol ethers with propylene glycol for removing sebum from the skin of a user without stinging and without dissolving and removing to any significant degree the intercellular lipids critical to the retention of moisture in the skin.

15 Claims, No Drawings

TONING COMPOSITION AND PROCESS OF USING

BACKGROUND OF THE INVENTION

The present invention relates to those compositions which are used for removing sebum from the skin and especially from the face of a user.

Presently-known compositions for removing sebum from the skin of a user typically employ from 30 to 60 percent by weight of one or more of ethanol, acetone, and isopropanol. Ethanol, acetone and isopropanol, however, tend to defat the skin and remove the intercellular lipids critical for retaining moisture in the skin. Further, the sebum that is removed is replaced in as few as two to three hours on average. These compositions also frequently cause an unpleasant stinging sensation when applied.

Compositions are also described in Swiss Patent No. 456,045 which employ aqueous solutions of water-soluble glycol ethers for removing sebum from the skin of a user in the treatment of acne. The glycol ethers are present in the compositions in significant amounts, for example at 20–50 percent by weight.

These glycol ether-based compositions are a vast improvement over the more typical alcohol- or acetone-based compositions, in that the glycol ethers dissolve sebum well and can provide for extended suppression of normal sebum levels, but do not dissolve the intercellular lipids in the skin or produce an unpleasant stinging sensation. One very significant drawback to the glycol ether-based toning compositions, however, is that at the levels of glycol ethers employed in the Swiss patent, these compositions have a disagreeable odor which is not easily masked by perfumes.

The consumer is faced, then, with choosing between a toning composition which tends to dry out the skin, which produces a stinging sensation and which is not particularly effective over time, and a composition which is effective for a longer period of time and which does not sting or dry out the skin of a user, but which stinks or which involves a strong masking scent. Neither option is particularly appealing.

SUMMARY OF THE INVENTION

The present invention solves this dilemma by providing a novel and improved toning composition which consists essentially of a) a glycol ether portion of one or more of the propylene and butylene oxide-based glycol ethers, b) propylene glycol and c) an inert carrier, typically water, with the glycol ether portion and propylene glycol being selected and proportioned with respect to one another so that they possess a combined solubility parameter in the range of from about 8 to about 11.

The toning composition of the present invention possesses the benefits associated with the use of glycol ethers rather than ethanol, isopropanol or acetone for dissolving sebum, but is effective at much lower concentrations of the glycol ethers and thus does not have the disagreeable odor associated with the compositions described in Swiss Patent No. 456,045.

DETAILED DESCRIPTION OF THE PREFERRED EMBODIMENTS

As briefly summarized above, the toning composition of the present invention consists essentially of a glycol ether portion, propylene glycol, and an inert carrier, with the glycol ether portion and propylene glycol together possessing a combined solubility parameter in the range of from about 8 to about 11.

The glycol ether portion is comprised of one or more of the propylene oxide- and butylene oxide-based glycol ethers. Exemplary of the propylene oxide-based glycol ethers are those presently sold by The Dow Chemical Company as the Dowanol TM PM (propylene glycol methyl ether, $CH_3(OC_3H_6)OH$, solubility parameter 10.1), Dowanol TM DPM (dipropylene glycol methyl ether, $CH_3(OC_3H_6)_2OH$, solubility parameter 9.3), Dowanol TM TPM (tripropylene glycol methyl ether, $CH_3(OC_3H_6)_3OH$, solubility parameter 8.7), Dowanol TM RCS (tetrapropylene glycol methyl ether, $CH_3(OC_3H_6)_4OH$, solubility parameter 8.0), Dowanol TM DPnB (dipropylene glycol n-butyl ether, $C_4H_9(OC_3H_6)_2OH$, solubility parameter 8.2), and Dowanol TM PnB (propylene glycol n-butyl ether, $C_4H_9(OC_3H_6)OH$, solubility parameter 8.9) glycol ethers.

Exemplary of the butylene oxide-based glycol ethers are butylene glycol methyl ether ($CH_3(OC_4H_8)OH$, solubility parameter 9.9), butylene glycol ethyl ether ($C_2H_5(OC_4H_8)OH$, solubility parameter 9.3), butylene glycol n-butyl ether ($C_4H_9(OC_4H_8)OH$, solubility parameter 9.0), dibutylene glycol methyl ether ($CH_3(OC_4H_8)_2OH$, solubility parameter 8.8), dibutylene glycol ethyl ether ($C_2H_5(OC_4H_8)_2OH$, solubility parameter 8.5), and dibutylene glycol n-butyl ether ($C_4H_9(OC_4H_8)_2OH$, solubility parameter 8.5).

Propylene glycol (solubility parameter 12.6) is widely available commercially, and merits little comment. The inert carrier is designed to act in the composition essentially as a diluent, and water is preferred.

As for the amounts of the various materials in the toner, the level of actives (e.g., the glycol ethers and propylene glycol) in the toner should generally be sufficient to remove certain amounts of sebum from the face of a user without being present in such amounts as to give rise to the disagreeable, difficult-to-mask odor associated with the glycol ether-rich compositions of Swiss Patent No. 456,045.

This odor appears to be associated with glycol ether levels of 5% by weight and above, based on the weight of the composition. Accordingly, the toning composition of the present invention preferably contains less than about 5% by combined weight of the propylene oxide- and butylene oxide-based glycol ethers.

The propylene glycol portion of the toner appears to a act cooperatively with the glycol ether portion in removing more sebum from the face of a user than would be removed using the glycol ether portion or the propylene glycol alone. As a result, glycol ether portion can be reduced to levels below the five weight percent threshold for odor that is suggested above without diminishing the sebum removal capacity of the toner overall. Propylene glycol, like the glycol ethers, also does not have the drawbacks associated with ethanol, isopropanol, acetone and the like.

The propylene glycol and glycol ethers are selected and employed in proportions so that these two parts of the toning composition define or possess a combined solubility parameter in the range of from about 8 to about 11. Given the solubility parameters of the glycol ethers and propylene glycol, the determination of what combinations and proportions may be employed within this range (without at the same time exceeding the five percent odor threshold for the glycol ether portion) is well within the abilities of one skilled in the art.

To obtain the benefits of the present invention in terms of sebum removal, it is considered that the propylene glycol and glycol ethers should further be selected so that a toning composition of the present invention preferably removes enough sebum from the face and especially the forehead of a user so that an initial sebumeter reading of less than about 250 micrograms per square centimeter, taken before application of the toner, is not recovered for at least about 4 hours on average after application.

More preferably, the toner is able to remove enough sebum so that an initial sebumeter reading of less than about 200 micrograms per square centimeter is not recovered on average until seven hours have elapsed since application. It should be noted that skin producing an initial 200 micrograms per square centimeter sebumeter reading is in the "oily" skin classification (180 to 230 or 240 micrograms per square centimeter), and embraces both normal skin (100–180 micrograms per square centimeter) and dry skin (less than 100 micrograms per square centimeter).

Most preferably, the toner will be fashioned so that an initial sebumeter reading of less than 200 micrograms per square centimeter is not recovered on average until eight hours have elapsed since application.

The overall amounts of glycol ethers and propylene glycol which will achieve such an eight-hour suppression may vary slightly depending on the glycol ethers used and the comparative levels of glycol ethers and propylene glycols in a toner, but as demonstrated by the examples below the glycol ether portion and propylene glycol ordinarily need not comprise more than about five percent by weight of the overall composition. This may be compared to the 20–50 percent by weight of glycol ethers specified by Swiss Patent No. 456,045.

While other materials need not be added to the toners of the present invention for sebum removal purposes, other conventional materials which do not materially affect the sebum removal performance of the toner could be added as desired. These other materials can be, for example, fragrances, surfactants for aiding in dissolving the fragrances in the toner, dyes, preservatives, antioxidants, pH adjusters and the like.

The toning composition of the present invention is usually made by mixing the glycol ethers, propylene glycol and water together, then adding any other materials such as of the type specified in the preceding paragraph to the combined water, propylene glycol and glycol ethers.

EXAMPLES

The present invention is more fully illustrated by the following Examples:

EXAMPLES 1

Artificial sebum was made by combining 26.3% by weight of oleic acid, 31.6% of tallow, 26.3% of cetyl palmitate, and 15.8% of squalene, using the composition of natural sebum described by Downing, *Journal of Investigative Dermatology*, vol. 53, no. 5, pp 322-7, as a guide.

The solubility of this material was determined in ethanol, acetone, isopropanol, and the above-described Dowanol TM PM, DPM, TPM, and RCS glycol ethers. The artificial sebum was soluble in each of the glycol ethers tested, and insoluble even above 40° C. (104° F.) in acetone. The mixture was soluble above 40° C. in both the ethanol and isopropanol, but precipitated out at lower temperatures.

EXAMPLE 2

To simulate intercellular lipids and to determine their solubilities in acetone, ethanol, isopropanol, and a propylene oxide-based glycol ether (Dowanol TM DPM glycol ether), a mixture of sodium oleate and sodium stearate was used as well as a glycosphingolipid mixture sold by George A. Hormel & Co. under the designation Dermatein GSL TM and conventionally used as a moisturizer. The mixture of sodium salts and glycosphingolipid mixture were both insoluble in the glycol ether, and soluble in the acetone, ethanol, and isopropanol.

EXAMPLES 3–13

For purposes of Examples 3–13 a series of aqueous toning compositions was prepared using various proportions and amounts of Dowanol TM DPM dipropylene glycol methyl ether ($CH_3(OC_3H_6)2OH$, solubility parameter 9.3) and propylene glycol. Each toner was applied to a single subject's forehead with a cotton wipe using a wiping motion, in each case just after obtaining an initial sebumeter reading. The initial sebumeter readings for the particular subject tested were in each case in the 170–180 micrograms per square centimeter range. Sebumeter readings were taken at 10 minutes, 30 minutes, and 1 hour after application and on an hourly basis thereafter until the initial sebumeter reading was reattained. The compositions, the solubility parameters of the combined glycol ether and propylene glycol materials in each composition, and the times required to reattain the initial, baseline reading for each composition are reported below in Table 1.

TABLE 1

| Composition (wt. percent) | 3 | 4 | 5 | 6 | 7 | 8 | 9 | 10 | 11 | 12 | 13 |
|---|---|---|---|---|---|---|---|---|---|---|---|
| Dowanol* DPM glycol ether | 0 | 10 | 20 | 30 | 38 | 40 | 22.5 | 15 | 7.5 | 3.75 | 0.75 |
| Propylene glycol | 40 | 30 | 20 | 10 | 2 | 0 | 7.5 | 5 | 2.5 | 1.25 | 0.25 |
| Triton X-100[a] surfactant | 1 | 1 | 1 | 1 | 1 | 1 | 1 | 1 | 1 | 1 | 1 |
| Water | 59 | 59 | 59 | 59 | 59 | 59 | 69 | 79 | 89 | 94 | 98 |
| Solubility Parameter | 12.6 | 11.78 | 10.95 | 10.13 | 9.47 | 9.3 | 10.13 | 10.13 | 10.13 | 10.13 | 10.13 |
| Time to Recover Baseline (hrs) | 6 | 7 | 8 | 8 | 8 | 7 | 8 | 8 | 8 | 8 | 7 |

[a]From Rohm & Haas, Philadelphia, PA

While preferred embodiments of the invention have been described and exemplified herein, numerous changes and modifications can be made thereto without departing from the intended scope of the invention, as expressed by the claims below.

What is claimed is:

1. A toning composition which consists essentially of:
   a glycol ether portion of one or more of the propylene and butylene oxide-based glycol ethers:

propylene glycol; and an inert carrier, wherein the glycol ether portion and propylene glycol are selected and proportioned so that the glycol ether portion and propylene glycol together define or possess a combined solubility parameter of from about 8 to about 11.

2. A toning composition as defined in claim 1, wherein the glycol ether portion and propylene glycol are selected and present in the toning composition in amounts whereby an initial sebumeter reading of less than about 250 micrograms per square centimeter, taken just prior to application of the astringent composition to a user's face, is not recovered for at least about four hours on average after such application.

3. A toning composition as defined in claim 1, wherein the glycol ether portion and propylene glycol are selected and present in the toning composition in amounts whereby an initial sebumeter reading of less than about 200 micrograms per square centimeter, taken just prior to application of the astringent composition to a user's face, is not recovered for about seven hours on average after such application.

4. A toning composition as defined in claim 1, wherein the glycol ether portion and propylene glycol are selected and present in the toning composition in amounts whereby an initial sebumeter reading of less than about 200 micrograms per square centimeter, taken just prior to application of the astringent composition to a user's face, is not recovered for about eight hours on average after such application.

5. A toning composition as defined in claim 1, wherein the glycol ether portion comprises less than about five percent by weight of the composition.

6. A toning composition as defined in claim 2, wherein the glycol ether portion comprises less than about five percent by weight of the composition.

7. A toning composition as defined in claim 3, wherein the glycol ether portion comprises less than about five percent by weight of the composition.

8. A toning composition as defined in claim 4, wherein the glycol ether portion comprises less than about five percent by weight of the composition.

9. A toning composition as defined in claim 1, wherein the glycol ether portion and propylene glycol together comprise five percent or less by weight of the toning composition.

10. A toning composition as defined in claim 2, wherein the glycol ether portion and propylene glycol together comprise five percent or less by weight of the toning composition.

11. A toning composition as defined in claim 3, wherein the glycol ether portion and propylene glycol together comprise five percent or less by weight of the toning composition.

12. A toning composition as defined in claim 4, wherein the glycol ether portion and propylene glycol together comprise five percent or less by weight of the toning composition.

13. A toning composition as defined in claim 1, wherein the glycol ether portion is comprised of one or more glycol ethers from the group consisting of propylene glycol methyl ether, dipropylene glycol methyl ether, tripropylene glycol methyl ether, tetrapropylene glycol methyl ether, propylene glycol n-butyl ether, dipropylene glycol n-butyl ether, butylene glycol methyl ether, butylene glycol ethyl ether, butylene glycol n-butyl ether, dibutylene glycol methyl ether, dibutylene glycol ethyl ether, and dibutylene glycol n-butyl ether.

14. A toning composition as defined in claim 1, wherein the inert carrier is water.

15. A process for removing sebum from the skin of a user, comprising the step of applying a toning composition as defined in any of claims 1-14 to the skin of such a user.

* * * * *